United States Patent
Overaker et al.

(10) Patent No.: US 6,478,681 B1
(45) Date of Patent: Nov. 12, 2002

(54) MAGNETIC COUPLINGS FOR IMPARTING SIMULTANEOUS ROTARY AND LONGITUDINAL OSCILLATIONS

(75) Inventors: Ronald F. Overaker, Durham, NC (US); Brian C. Dodge, Durham, NC (US); Robert Machemer, Durham, NC (US); Cynthia A. Toth, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/721,775

(22) Filed: Nov. 27, 2000

(51) Int. Cl.$^7$ ............................................... F16D 27/01
(52) U.S. Cl. ........................................ 464/29; 74/22 R
(58) Field of Search .............. 464/29, 162; 403/DIG. 1; 74/22 R, 23; 606/171

(56) References Cited

U.S. PATENT DOCUMENTS

| | | | |
|---|---|---|---|
| 1,043,573 A | * | 11/1912 | Keller et al. ................. 74/22 R |
| 2,067,819 A | * | 1/1937 | Bell ........................... 74/22 R |
| 4,314,560 A | | 2/1982 | Helfgott et al. |
| 4,420,851 A | * | 12/1983 | Wiener ....................... 74/22 R |
| 4,441,061 A | | 4/1984 | Yoshida et al. |
| 4,504,264 A | | 3/1985 | Kelman |
| 4,696,298 A | | 9/1987 | Higgins et al. |
| 4,753,234 A | | 6/1988 | Martinez |
| 4,827,615 A | | 5/1989 | Graham |
| 4,986,827 A | | 1/1991 | Akkas et al. |
| 5,047,008 A | | 9/1991 | de Juan, Jr. et al. |
| 5,133,729 A | | 7/1992 | Sjostrom |
| 5,152,744 A | | 10/1992 | Krause et al. |
| 5,222,959 A | | 6/1993 | Anis |
| 5,269,794 A | | 12/1993 | Rexroth |
| 5,322,505 A | | 6/1994 | Krause et al. |
| 5,376,078 A | | 12/1994 | Dinger, III et al. |
| 5,381,576 A | | 1/1995 | Hwang |
| 5,411,513 A | | 5/1995 | Ireland et al. |
| 5,490,860 A | | 2/1996 | Middle et al. |
| 5,492,527 A | | 2/1996 | Glowa et al. |

(List continued on next page.)

FOREIGN PATENT DOCUMENTS

| | | | | |
|---|---|---|---|---|
| RU | 1453-524 A | | 1/1989 | |
| RU | 2003886 C1 | * | 11/1993 | ................. 464/29 |
| SU | 1453-524 A | * | 1/1989 | ................. 74/22 R |

Primary Examiner—Greg Binda
(74) Attorney, Agent, or Firm—Nixon & Vanderhye P.C.

(57) ABSTRACT

Magnetic couplings impart simultaneous reciprocal rotary and longitudinal motions or oscillations to a work element. In preferred embodiments, the magnetic couplings include a drive shaft, an output shaft coaxially aligned with the drive shaft relative to a central axis, and drive and driven magnet assemblies connected operatively to the drive and output shafts, respectively. The drive and driven magnet assemblies include permanent magnets arranged to translate continuous rotation of the drive shaft into simultaneous rotary and longitudinal movements of the driven magnet assembly relative to the drive axis. A resilient support member exhibiting torsional and longitudinal resiliency (e.g., an annular elastomeric disc) is most preferably operatively connected to the output shaft to allow for such simultaneous rotary and longitudinal movements thereof.

25 Claims, 9 Drawing Sheets

U.S. PATENT DOCUMENTS

| | | |
|---|---|---|
| 5,492,528 A | 2/1996 | Anis |
| 5,510,070 A | 4/1996 | Krause et al. |
| 5,592,727 A | 1/1997 | Glowa et al. |
| 5,593,415 A * | 1/1997 | Adrian .................. 606/171 X |
| 5,602,449 A | 2/1997 | Krause et al. |
| 5,609,602 A | 3/1997 | Machemer et al. |
| 5,618,293 A | 4/1997 | Sample et al. |
| 5,672,945 A | 9/1997 | Krause |
| 5,690,641 A | 11/1997 | Sorensen et al. |
| 5,707,350 A | 1/1998 | Krause et al. |
| 5,712,543 A | 1/1998 | Sjostrom |
| 5,717,266 A | 2/1998 | Maynard, Jr. |
| 5,722,945 A | 3/1998 | Anis et al. |
| 5,730,718 A | 3/1998 | Anis et al. |
| 5,747,953 A | 5/1998 | Philipp |
| 5,749,885 A | 5/1998 | Sjostrom et al. |
| 5,794,295 A | 8/1998 | Shen |
| 5,807,401 A | 9/1998 | Greishaber et al. |
| 5,827,292 A | 10/1998 | Anis |
| 5,871,492 A | 2/1999 | Sorensen |
| 5,873,885 A | 2/1999 | Weidenbenner |
| 5,911,699 A | 6/1999 | Anis et al. |
| 5,916,229 A | 6/1999 | Evans |
| 5,941,876 A | 8/1999 | Nardella et al. |
| 5,980,546 A | 11/1999 | Hood |
| 6,004,284 A | 12/1999 | Sussman et al. |
| 6,077,285 A | 6/2000 | Boukhny |
| 6,184,636 B1 | 2/2001 | Lewis et al. |

* cited by examiner

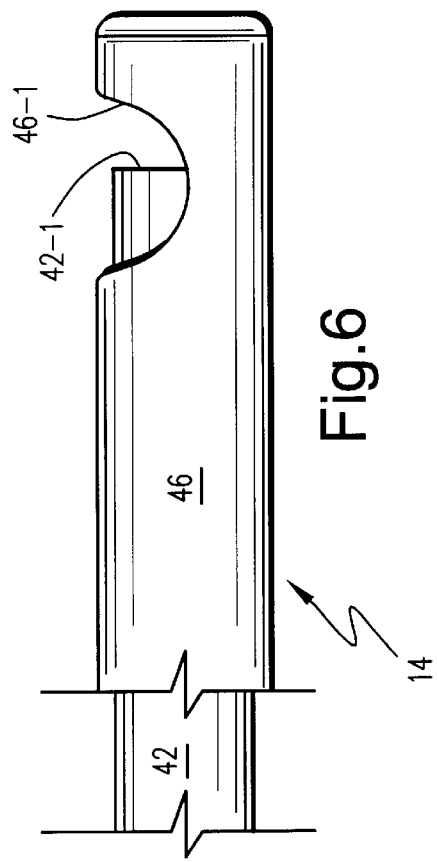
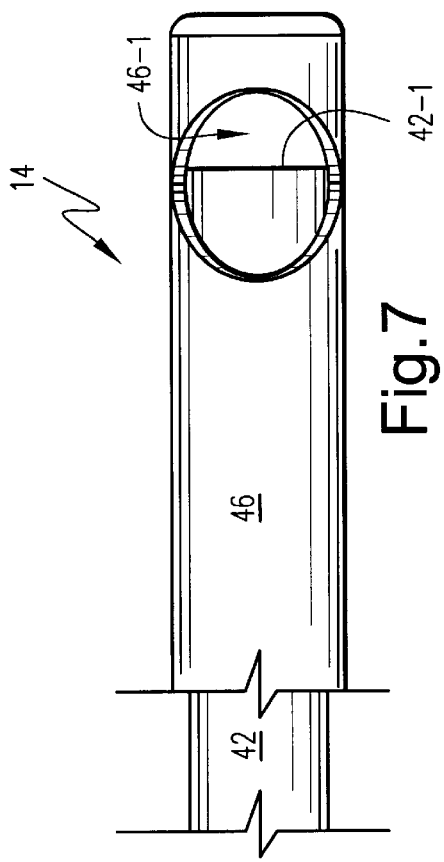
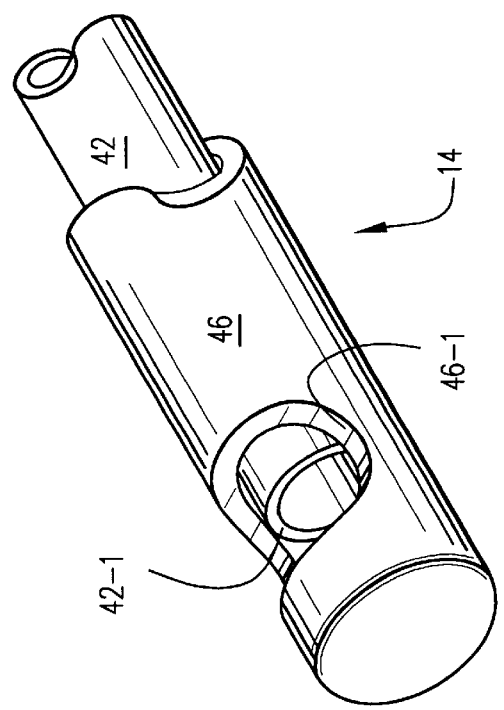

MAGNETIC COUPLINGS FOR IMPARTING SIMULTANEOUS ROTARY AND LONGITUDINAL OSCILLATIONS

FIELD OF THE INVENTION

The present invention relates generally to couplings and methods for imparting simultaneous rotary and longitudinal oscillations to a work piece, for example, a distal element associated operatively with a surgical instrument. In preferred forms, the present invention is embodied in couplings and methods for surgical instruments (e.g., ophthalmic microsurgical instruments) so as to achieve relatively high frequency simultaneous rotary (angular) and longitudinal (linear) oscillations relative to the elongate axis of the surgical instrument's work piece.

BACKGROUND OF THE INVENTION

During ophthalmic microsurgery, such as lens removal, instruments are used with either horizontal or axial oscillatory movements. Conventional horizontal or axial oscillatory instruments using piezoelectric technology tend to create heat during surgical procedures which might cause indirect damage to adjacent ocular tissues.

Recently, U.S. Pat. No. 5,609,602 to Machemer et al (the entire content of which is expressly incorporated hereinto by reference) disclosed a relatively high frequency rotary oscillatory coupling which includes a pair of opposed hubs which are independently rotatable about a common axis. Pairs of permanent magnets are provided in the opposed faces of the hubs. Thus, when the proximal hub is continuously rotated in a selected rotational direction by a suitable drive motor, the distal hub will be caused to rotate in that same rotational direction. The distal hub, however, is prevented from rotating a complete rotary cycle and instead reverses its rotary direction with the assistance of a spring member 30. Thus, the continual reversal of the rotary direction of the distal hub will cause oscillatory rotary movement to be imparted to a distal element (e.g., associated operatively with a surgical instrument).

U.S. Pat. No. 5,717,266 to Maynard, Jr. (the entire content of which is expressly incorporated hereinto by reference) discloses an oscillatory drive having a driven rotor that is mounted on a shaft and includes plural driven permanent magnets disposed thereon. A spring arrangement is coupled to the driven rotor and limits both clockwise and counterclockwise rotation. First and second driving rotors are mounted on the shaft on one and another sides of the driven rotor. The drive mechanism is such that spring-limited oscillatory rotary movements reciprocally in the clockwise and counterclockwise directions are imparted to the driven rotor. The structures of the Maynard, Jr. '266 patent, however, appear incapable of imparting both rotary and longitudinal oscillations to the driven rotor.

There are a number of prior proposals for imparting simultaneous torsional and longitudinal oscillations to a medical handpiece tip, as shown in U.S. Pat. No. 4,504,264 to Kelman, U.S. Pat. No. 5,911,699 to Anis et al, U.S. Pat. No. 5,722,945 to Anis et al and U.S. Pat. No. 6,077,285 to Boukhny (the entire content of each patent being expressly incorporated hereinto by reference). IN this regard, the Kelman '264 patent discloses a hand-held surgical instrument having a working tip which, in addition to longitudinal high frequency vibration, is also capable of comparatively low frequency lateral oscillations. The Anis et al '699 and Anis et al '945 patents each disclose a medical handpiece having a fragmenting surface formed at a working tip which is simultaneously rotated and reciprocated ultrasonically so that tissue is fragmented. The Boukhny '285 patent discloses a medial handpiece having two sets of piezoelectric elements which are polarized to produce longitudinal and torsional motion.

SUMMARY OF THE INVENTION

Broadly, in one aspect, the present invention is embodied in magnetic couplings which simultaneously impart reciprocal rotary and longitudinal motions or oscillations to a work element. In preferred embodiments, the magnetic couplings of the present invention are comprised of a drive shaft, an output shaft coaxially aligned with the drive shaft relative to a central axis, and drive and driven magnet assemblies connected operatively to the drive and output shafts, respectively. The drive and driven magnet assemblies include permanent magnets arranged to translate continuous rotation of the drive shaft into simultaneous rotary and longitudinal movements of the driven magnet assembly relative to the drive axis. In this regard, the drive magnet assembly most preferably includes at least one pair of permanent magnets circumferentially spaced-apart and longitudinally staggered relative to one another. This circumferential and longitudinal separation thus cooperatively effects the movement of the permanent magnets of the driven magnet assembly to cause movements in both the circumferential and longitudinal directions. Thus, the arrangement of the permanent magnets of the drive magnet assembly is such to create a magnetic "cam" of sorts which affects the movements of the driven magnet assembly.

Most preferably, a resilient support member exhibiting torsional and longitudinal resiliency (e.g., an annular elastomeric disc) is operatively connected to the output shaft to allow for such simultaneous rotary and longitudinal movements thereof. In addition, the resilient support member establishes limits on the extent of rotary and longitudinal movements of the driven magnet assembly thereby allowing for simultaneous reciprocal oscillations in both rotational and longitudinal directions.

Surgical instruments of the present invention which employ such magnetic couplings will typically include a distal work element which connected to the driven magnet assembly so as to be capable of reciprocal simultaneous movements in both rotational and longitudinal directions relative to the work element's central axis. Most preferably, therefore, the surgical instrument is hand-held and will include a drive motor which is connected operatively to a drive shaft so as to impart continuous rotational motion to the drive magnet assembly.

It would also be highly desirable, particularly in the field of surgical instruments, if a power supply could be provided to minimize any net torque and/or vibration on a drive assembly and hence the instrument itself (e.g., so as to minimize (if not eliminate entirely) noticeable movements of the surgical instrument that might adversely affect the attending surgeon's manipulation of the instrument). According to another aspect of the present invention, a power supply which addresses such a need is also provided.

In this regard, the preferred power supply in accordance with the present invention minimizes any net torque and/or vibration produced on a drive assembly. In especially preferred embodiments, the power supply of the present invention comprises a control circuit which controls the angular velocity of a drive assembly (e.g., the motor and drive magnet assembly) so that its angular velocity is maintained at a constant level. Preferably, the control circuit is capable of quickly adjusting the angular velocity of the drive assembly back to the constant level if the rotational speed of drive assembly were to deviate therefrom because of, for example, a force load imposed on the drive assembly. Most preferably, this adjustment is accomplished in less time as compared to the time required for one rotation of the drive assembly to thus minimize any net torque and/or vibration thereon.

These and other aspects and advantages will become more apparent after careful consideration is given to the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein;

FIGS. 5–7 are perspective, side elevational and top plan views, respectively, of one possible configuration for a working element that may be employed in the surgical instrument of the present invention;

DETAILED DESCRIPTION OF THE INVENTION

Figure 1:
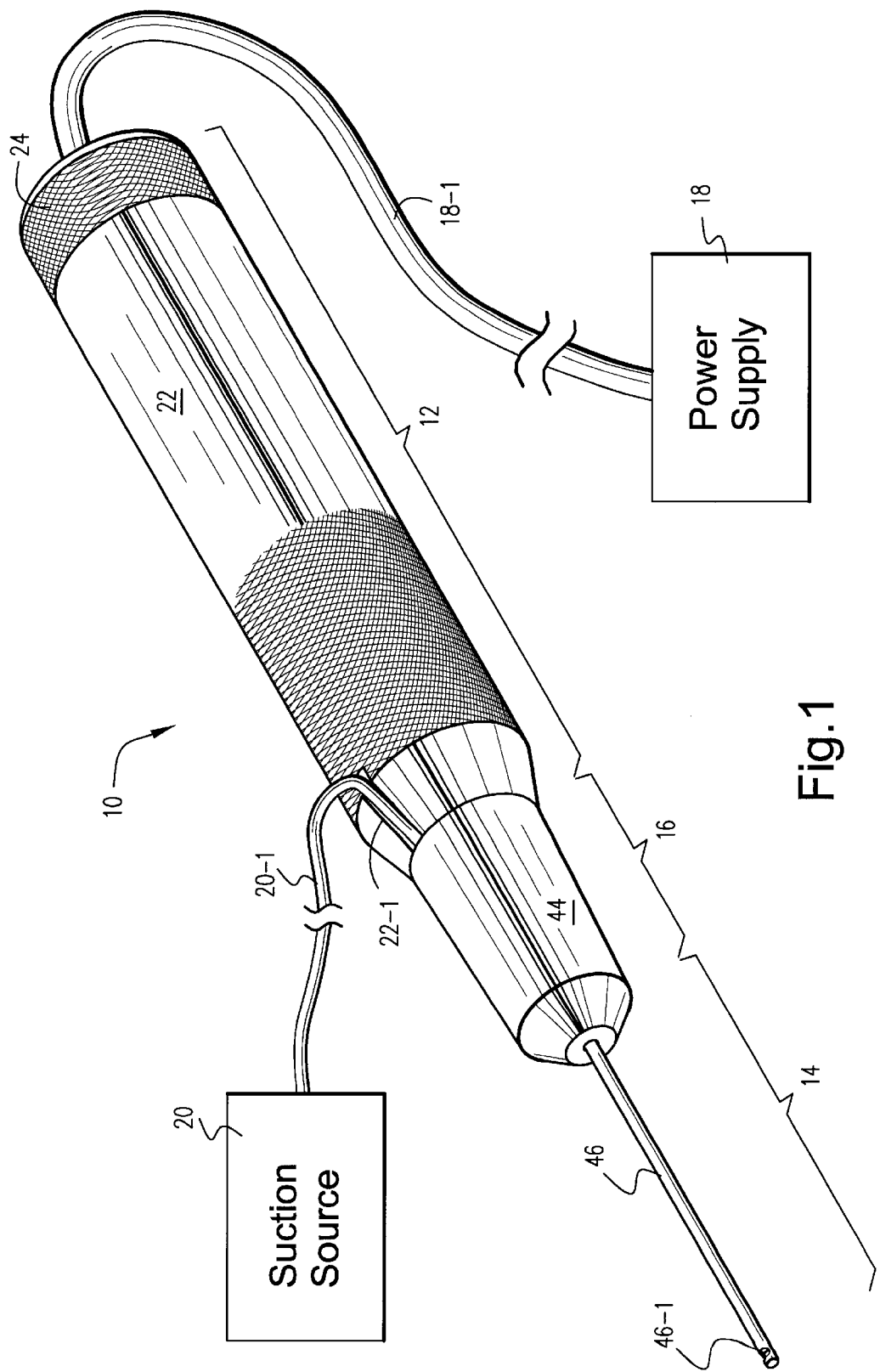
FIG. 1 is a perspective view of one particularly preferred embodiment of a surgical instrument in accordance with the present invention.

A particularly preferred embodiment of a surgical instrument 10 in accordance with the present invention is depicted in accompanying FIG. 1. As shown, the surgical instrument 10 essentially includes a proximal handle section 12, a distal axially elongate working tool section 14, and a coupling section 16 intermediate of, and coupling, the handle and working tool sections 12, 14, respectively. Electrical power is supplied to the instrument 10 via a power cable 18-1 and its associated power supply 18 (a more detailed description of which appears below). A suction source 20 is in fluid-communication (via flexible tubing 20-1 with the lumen of tube 42 that is within the tool section 14) with working tip 46-1. This allows biological material to be aspirated through the working tip 46-1 thereof and removed from the operating field. Alternatively, of course, the suction source 20 may if desired be replaced by a fluid source so that the surgical field may be irrigated (e.g., with saline solution) through the tubing 20-1 and then on to the tip 46-1 of the tool section 14.

Figure 2:
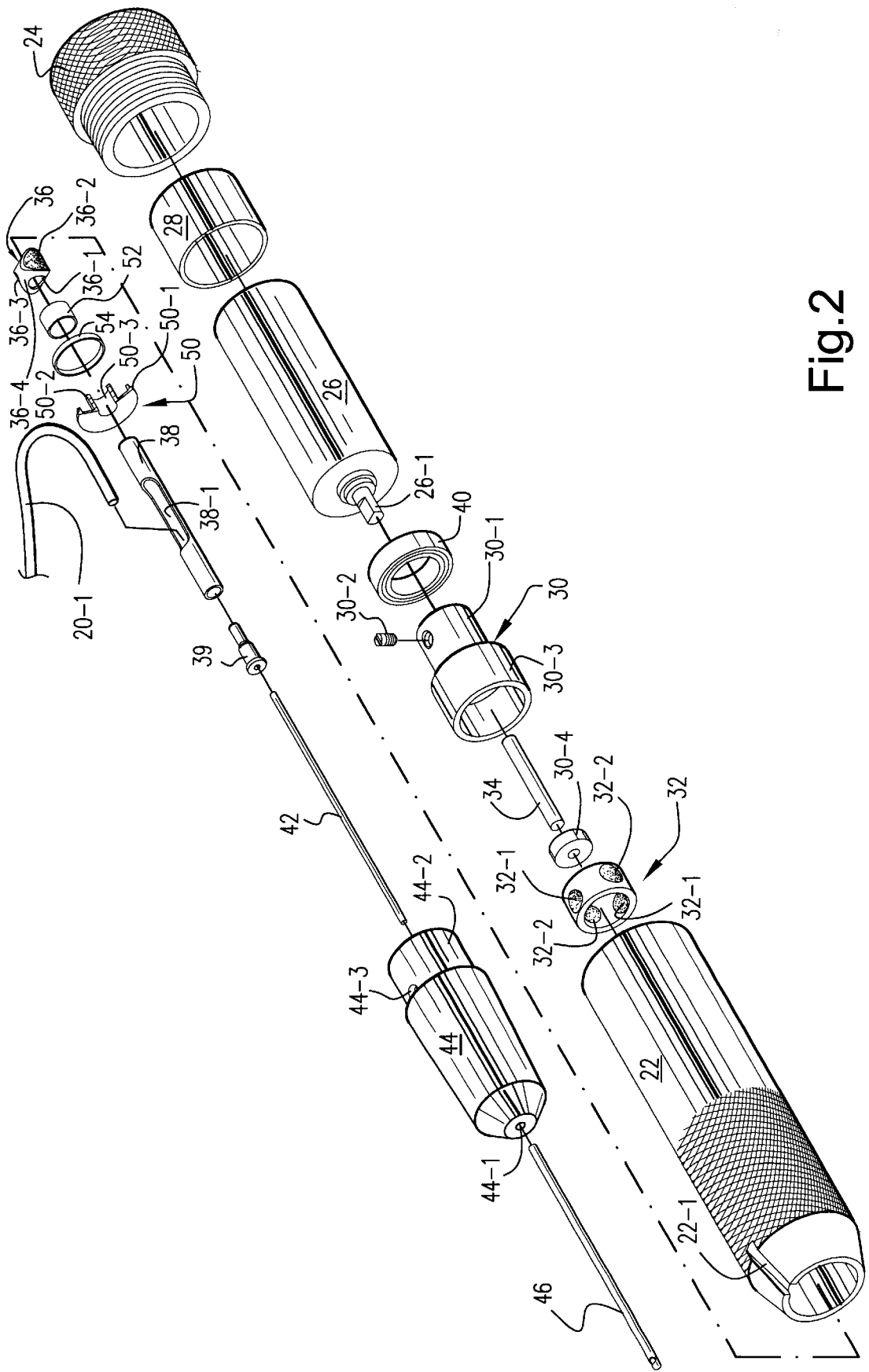
FIG. 2 is an exploded perspective view of the principal structural components employed in the surgical instrument depicted in FIG. 1.
Figure 3:
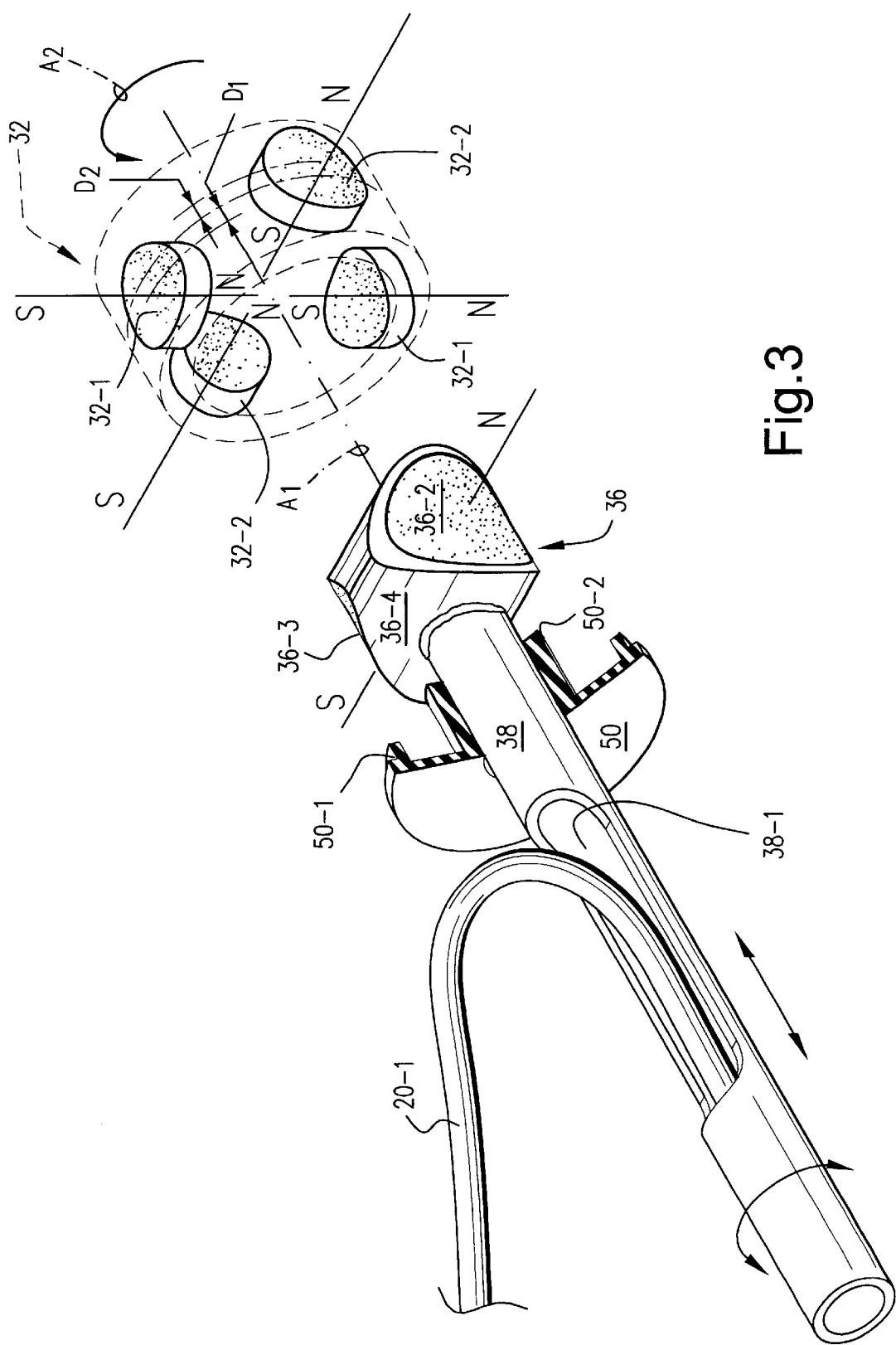
FIG. 3 is an enlarged exploded perspective view of the magnetic coupling assembly in accordance with the present invention.
Figure 4:
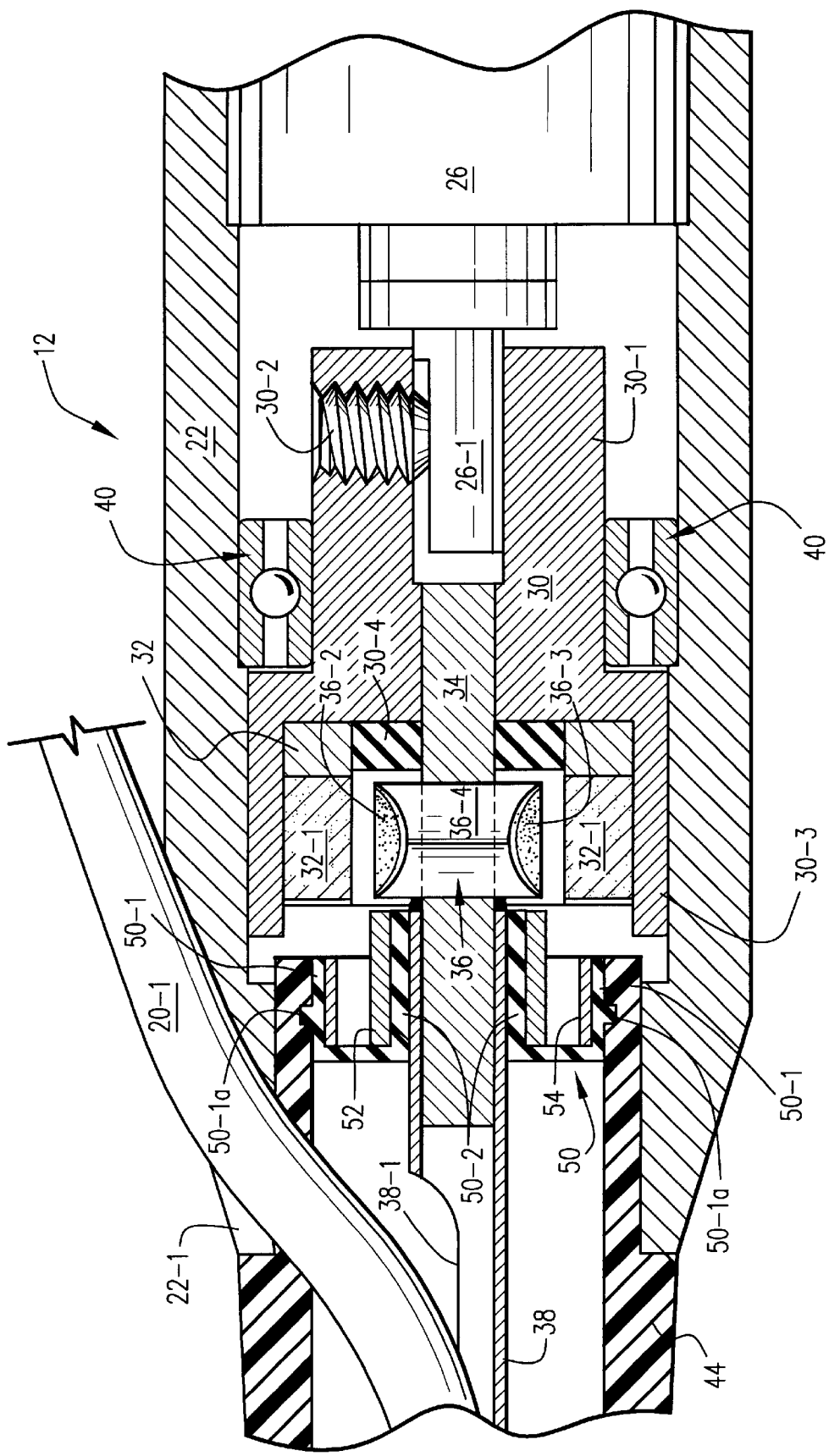
FIG. 4 is an enlarged cross-sectional elevational view of the coupling assembly in accordance with the present invention.

The various components of the surgical instrument 10 are perhaps more clearly visible in accompanying FIGS. 2–4. In this regard, the handle section 12 includes a tubular handle member 22 which threadably receives an end cap 24 so as to close its proximal end. The interior of the handle member 22 houses a motor 26 having a rotary drive shaft 26-1 extending distally therefrom in coaxial alignment with the longitudinal axis of the instrument 10. The relative position of the motor 26 within the handle member 22 is maintained by a spacer ring 28 positioned within the interior of the end cap 24.

A drive hub 30 has a proximal stem 30-1 which is sleeved over the drive shaft 26-1 and is rigidly interconnected thereto by means of a set screw 30-2. The drive hub 30 also has a distal retaining cup 30-3 having a distally open end. A drive magnet ring 32 which carries pairs of first and second permanent magnets 32-1 and 32-2, respectively, is immovably fixed into the open end of the retaining cup 30-3. A proximal end portion of a bearing pin 34 is also immovably fixed into the proximal stem 30-1 of the drive hub 30. As is seen in FIGS. 2 and 3, the central aperture 36-1 of the driven magnet assembly 36 is coaxially aligned with the lumen of the distally located transition tube 38. Thus, the distal end portion of the bearing pin 34 extends coaxially outwardly from the open end of drive hub 30 through the central aperture 36-1 of the driven magnet assembly 36 and is rotatably received within a proximal region of the hollow lumen defined by the elongate transition tube 38 (see FIG. 4).

The magnet assembly 36 includes a rod-shaped permanent magnet having exposed arcuately shaped north and south pole faces 36-2 and 36-3, respectively, fixedly embedded within the exterior tubular housing 36-4. The central aperture 36-1 thus extends transversely through the rod-shaped permanent magnet and the housing 36-4 in which it is embedded.

A bearing ring assembly 40 is sleeved over the proximal stem 30-1 of the drive hub 30 so as to facilitate its rotation within the handle member 22. Specifically, by virtue of the rigid interconnection between the proximal stem 30-1 and the drive shaft 26-1 of the motor 26, the entire drive hub 30 will be rotated continuously in a rotational direction. Since the drive magnet ring 32 and the bearing pin 34 are each immovably fixed to the drive hub 30, they will likewise be rotated in the same rotational direction as the drive hub 30.

The elongate hollow transition tube 38 is rigidly bonded to the housing 36-4 of the driven magnet assembly 36 so that the lumen of the tube 38 is in coaxial alignment with the central aperture 36-1. As a result, the driven magnet assembly 36 and the transition tube 38 are moveable as a unit simultaneously in rotary and longitudinal oscillations about and along, respectively, the central elongate axis of the surgical instrument 10 as will be described in greater detail below. During such rotary and longitudinal oscillations, the driven magnet assembly 36 is supported by the bearing pin 34. In order to dampen vibrations of the driven magnet assembly 36 (particularly during its reciprocal rectilinear oscillations), an elastomeric washer 30-4 is positioned within the drive magnet ring 32 against the base of the retaining cup 30-3.

A bushing 39 is immovably fixed to the distal end of the transition tube 38. A proximal end of a rigid working tube 42 is, in turn, immovably fixed to the bushing 39. The proximal end of the bushing 39 is fluid-connected to the terminal end of the flexible tubing 20-1 which enters the lumen of the transition tube 38 distally of the bearing pin 34 via an axially elongate slot 38-1. The tubing 20-1 extends in the proximal direction through an entrance slot 22-1 formed in the handle member 22 and then on to the suction source 20 (see FIG. 1).

The tool section 14 is generally comprised of a closure hub 44 and an outer rigid working tube 46 immovably fixed to, and thus distally extends from, the opening 44-1 in hub 44. Thus, the interior working tube 42 is moveably received within the outer working tube 46 so that the latter is sleeved over the former. The proximal flange 44-2 is itself immovably fixed to the distal end of the handle member 22 and includes an opening 44-3 through which the flexible tubing 20-1 may extend so as to be fluid-connected with the bushing 39 as described previously. The distal tip of the outer tube 46 includes an opening 46-1 which cooperates with the distal tip of the inner tube 42, the purpose of which will be described in greater detail below.

Important to the present invention is the presence of a resilient coupling between the moveable transition tube 38 and the stationary closure hub 44. In the preferred embodiment of this invention depicted in the accompanying drawing FIGS. 1–4, such resilient coupling includes a resilient disc-shaped coupling 50 which allows for both rotary and longitudinal oscillations of the tube 38 (and hence the interior working tube 42 immovably fixed thereto). In this regard, the resilient coupling 50 most preferably is formed as a one-piece structure from an elastomeric material (e.g., silicone rubber, butyl rubber or the like) and includes an outer flange 50-1 and an inner flange 50-2 which defines an interior cylindrical opening 50-3. As is perhaps more clearly shown in FIG. 4, the proximal end portion of the transition tube 38 is received within the interior opening 50-3 and is rigidly bonded thereto by a suitable bonding adhesive. An interior retaining ring 52 is compressively sleeved over the interior flange 50-2 to ensure that it remains immovably fixed to the transition tube 38. In a similar manner, the outer flange 50-1 is bonded to an interior surface region of the closure hub 44 by a suitable bonding adhesive. An annular rib 50-1a is also provided along with an outer retaining- ring 54 to ensure that the outer flange 50-1 remains immovably fixed to the interior of the closure hub 44. As can be appreciated, the resilient coupling 50 is both torsionally and longitudinally resiliently flexible relative to the elongate axis of the surgical instrument 10.

The enlarged exploded view provided by accompanying FIG. 3 provides a pictorial representation of the manner in which the magnetic coupling of the present invention functions. In this regard, it will be appreciated, of course, that the drive magnet ring 32 is coaxially positioned in surrounding relationship to the driven magnet assembly 36 so that a small, but meaningful, gap is presented therebetween. In such a manner, the latter is free to move relative to the former.

As is evident from FIG. 3, the magnet pairs 32-1 and 32-2 are longitudinally off-set relative to one another. Specifically, each of the magnets forming the magnet pair 32-1 is disposed in a plane passing transverse to the elongate axis (A1) of the instrument 10 which is offset distally a dimension D1 relative to a central transverse plane of the magnet ring 32. On the other hand, each of the magnets forming the magnet pair 32-2 is disposed in a transverse plane which is off-set proximally from the central transverse plane of the magnet ring 32 by a dimension D2. Thus, the magnet pairs 32-1 and 32-2 are off-set in the longitudinal direction of axis A1 by the sum of dimensions D1 and D2.

In use, therefore, the magnet ring 32 may be rotated continuously (e.g., by virtue of the driven interconnection with the drive shaft 26-1 of the motor 26 through the drive hub 30 as described previously) in a direction indicated in FIG. 3 by arrow A2. (Of course, an opposite rotational direction may be imparted to the magnet ring 32, if desired. However, for purpose of discussion, it will be assumed here that rotation is imparted to the magnet ring 32 in the direction of arrow A2.) The magnetic fields associated with the magnet pairs 32-1 and 32-2 will therefore periodically be magnetically coupled and decoupled to the poles of magnets 36-2, 36-3 of the driven magnet assembly 36. Thus, rotation of the driven magnet assembly 36 in the same direction as arrow A2 will result thereby also rotating the tube 38 and the interior working tube 42 operatively attached thereto. Since the resilient coupling 50 is immovably fixed to both the transition tube 38 and the closure hub 44, it will exert a resilient torsional force to the driven magnet assembly 36 which, at some point during rotation of the driven magnet assembly 36, will cause magnetic decoupling to occur with the magnet ring 32. At that time, the driven magnet assembly 36 will then rotate about the axis A1 in a direction opposite to arrow A2. Of course, continued rotation of the magnet ring 32 about the magnet assembly 36 will cause the latter to rotationally oscillate about the axis A1.

Simultaneously with such rotational oscillations, the magnetic force interactions between the drive magnet ring 32 and the driven magnet assembly 36 will cause the latter to be moved reciprocally longitudinally along the axis A1. That is, both simultaneous rotational and longitudinal oscillations are imparted to the driven magnet assembly 36 (and the structures fixed thereto, for example, the transition tube 38 and the interior working tube 42) by virtue of the continuous rotational motion of the drive magnet ring 32. Such reciprocal longitudinal oscillations are assured by the longitudinal off-set between the magnet pairs 32-1, 32-2 associated with the drive magnet ring 32. Thus, the positions of the permanent magnet pairs 32-1, 32-2 in the drive magnet ring 32 will effectively create a magnetic "cam" that imparts simultaneous rotary and longitudinal movements relative to the elongate axis A1 of the instrument 10. Moreover, the arrangement of more (or less) magnet pairs, their relative spacing, the arrangement of their magnetic poles and/or the rotational speed of the magnet ring 32 will allow those skilled in the art to achieve a wide range of motion profiles which may be imparted to the working tube 42, for example.

It should be understood that, as used herein and in the accompanying claims, the terms "oscillations" and/or "oscillate" mean to move reciprocally between two extreme positions. Thus, in accordance with the present invention, those structures which are immovably fixed to the driven magnet assembly 36 are caused to oscillate simultaneously in both rotary and longitudinal directions relative to the elongate axis A1.

The resilient elastomeric coupling 50 serves several beneficial functions. For example, as described above, the coupling 50 serves to store energy and release it for very fast movement to the working tube 42 in both the axial and rotary directions. In addition, the coupling 50 serves to physically seal the proximally located components within the handle 12 against contamination by foreign matter.

Although the resilient coupling 50 has been shown and described above with reference to FIGS. 1–4 as being generally a flat, disc-shaped, unitary elastomeric member, virtually any other geometric design may be employed satisfactorily to achieve "engineered" movements as may be desired by the instrument designer. Thus, the disc-shaped resilient coupling 50 is advantageous in that it provides for more motion in an axial direction as compared to motion in a rotary direction. However, as shown in accompanying FIGS. 4A and 4B, resilient couplings 50A and 50B, respectively, may be provided with a generally conically-shaped section. It will, of course, be understood that many of the structural components depicted in FIG. 4 are likewise present in the embodiments of FIGS. 4A and 4B, but have been omitted therein for the purpose of clarity of presentation.

Figure 4A:
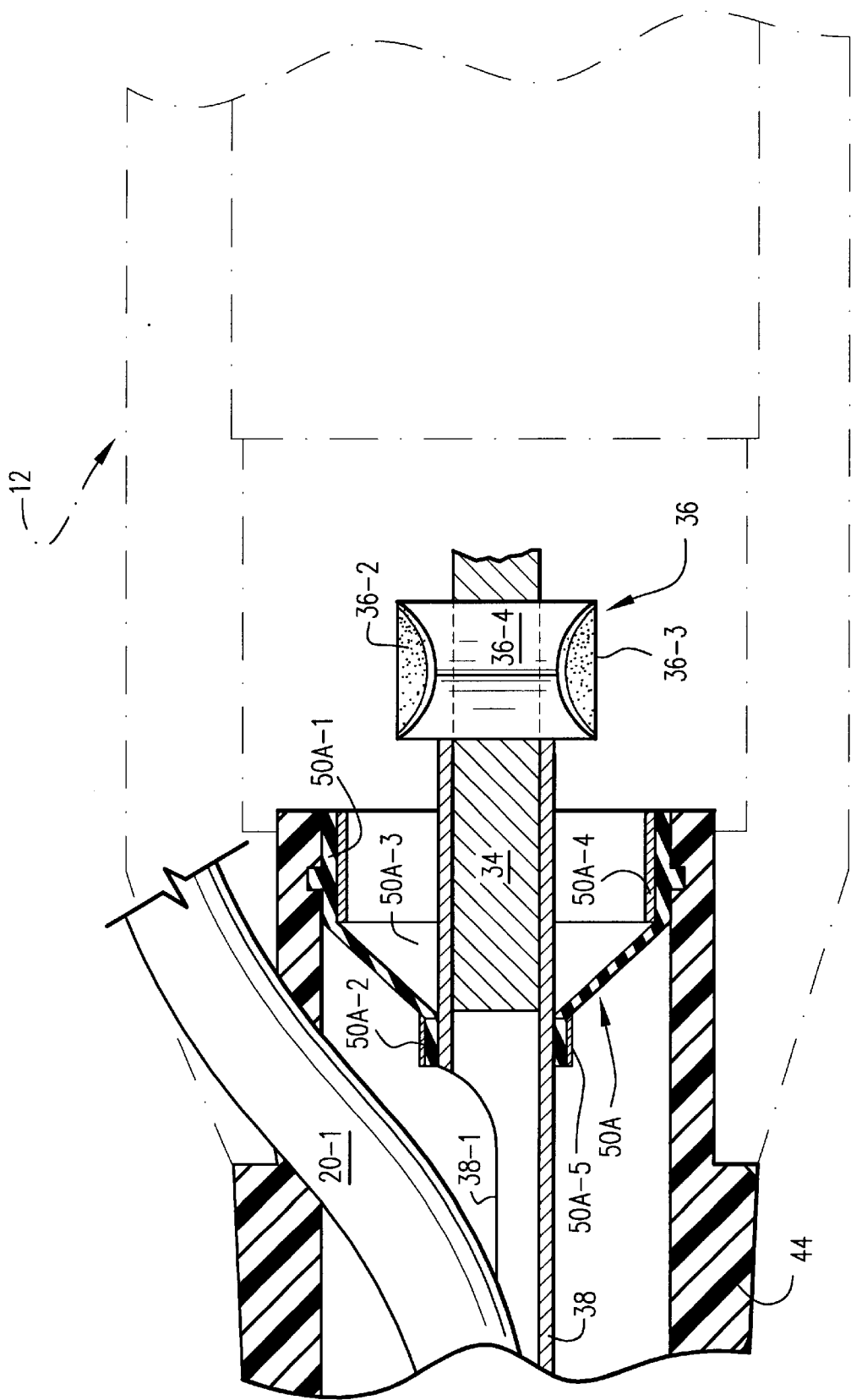
FIGS. 4A and 4B are each enlarged cross-sectional elevational views of a part of the coupling assembly in accordance with the present invention and respectively illustrate other possible embodiments of the resilient coupling that may be used therein.

As shown in FIG. 4A, for example, a coupling 50A may be provided unitarily with cylindrical base and neck sections 50A-1, 50A-2, respectively, and a generally conically shaped transition section 50A-3. The base and neck sections 50A-1 and 50A-2, may be fixed to the closure hub 44 and transition tube 38 via retaining rings 50A-4 and 50A-5, respectively.

Figure 4B:
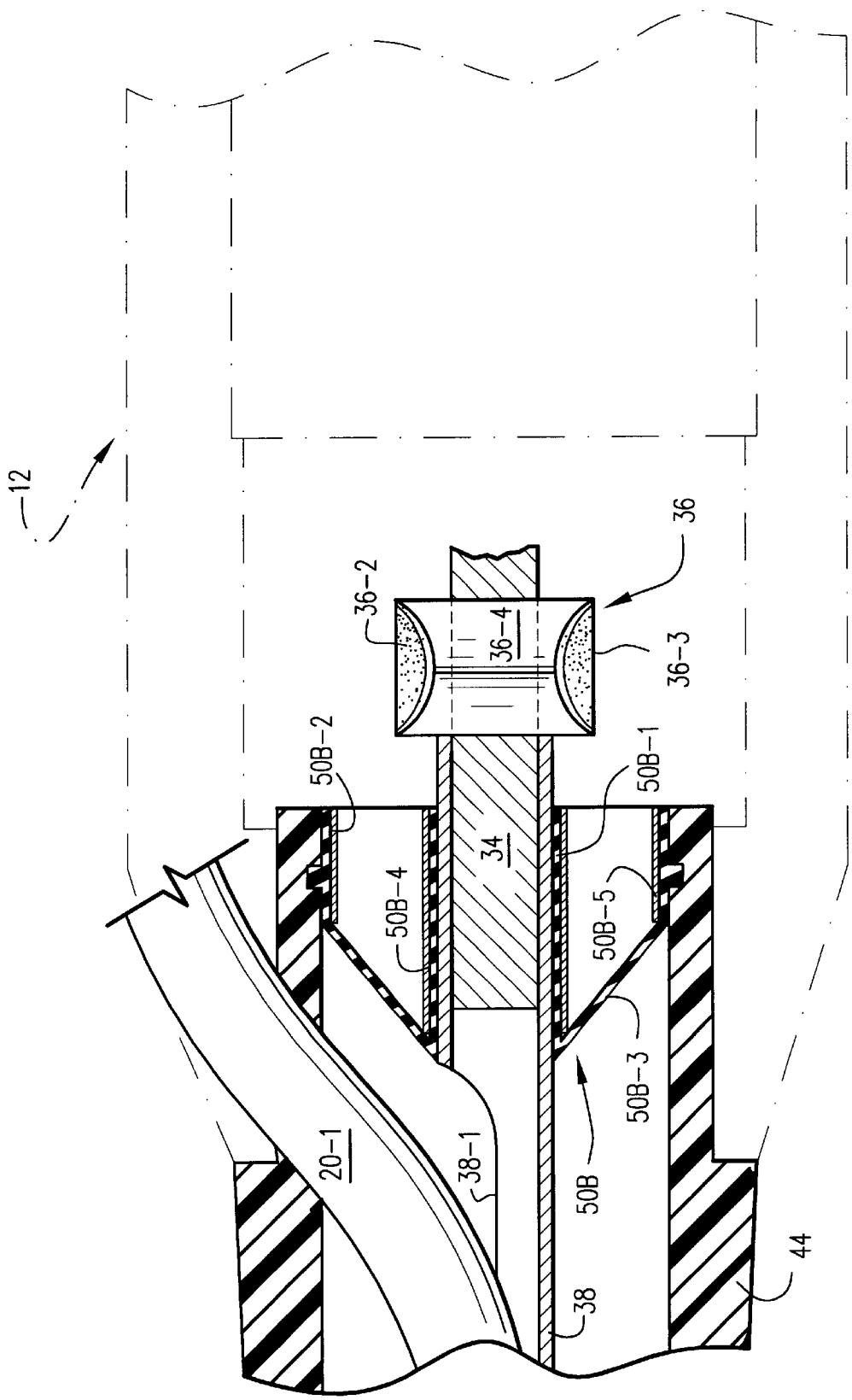

Accompanying FIG. 4B shows another embodiment of a resilient coupling 50B that may be employed in the practice of the present invention. As shown, the coupling 50B has concentrically disposed cylindrical (tubular) inner and outer sections 50B-1, 50B-2, respectively, which are unitarily joined to one another at their distal ends by a generally conically shaped transition section 50B-3. The cylindrical inner and outer sections are fixed to the transition tube 38 and the closure hub 44 by means of retaining rings 50B-4 and 50B-5, respectively.

The general conical shapes of the transition sections 50A-3 and 50B-3 of the resilient coupling 50A and 50B thereby allow the instrument designer to impart greater propensity of movement in a rotary direction. The angle of the conical shape, its cross-section and the durometer of the elastomeric material from which it is made contribute to the ultimate motions that are achieved. Thus, as the angle of the conical shape approaches zero degrees (i.e., a tubular shape), the motion is essentially mostly in a rotary direction. By varying the angle of the conical shape, one may alter desirably the motion imparted to the working tube 42. Moreover, the diameter (with constant cross-sectional area) controls the ratio of torsional to axial stiffness. That is, a large diameter thin wall tube is stiffer in torsion than a small diameter tube with the same cross-sectional wall area. Thus, within these parameters, an instrument designer can "engineer" virtually any type of axial and rotary oscillations that may be desired.

As those in this art can also appreciate, the simultaneous rotary and longitudinal oscillations achieved by the present invention can be employed to usefully move a variety of work elements. For example, as shown in FIGS. 5–7, one embodiment of the working tip 14 includes a generally hemispherically shaped opening 46-1 formed in the outer working tube 46 which exposes a terminal edge 42-1 of the interior working tube 42. In this manner, the edge 42-1 serves as a cutter (i.e., by virtue of the rotary and longitudinal oscillations imparted thereto by the magnetic coupling described previously) which allows biological material to be removed from a patient (e.g., an ocular lens, or vitreous, during ophthalmic surgery) and aspirated through the opening 46-1 and the interior lumen of the tube 42 via suction tube 20-1 and its associated suction source 20. The edge 42-1 may be sharpened, serrated or provided with an abrasive material as might be needed for particular surgical procedures.

Figure 9:
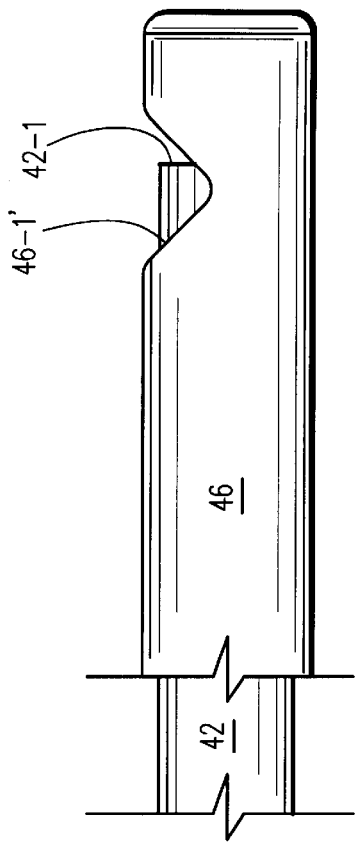
FIGS. 8–10 are perspective, side elevational and top plan views, respectively, of another possible configuration for a working element that may be employed in the surgical instrument of the present invention.
Figure 10:
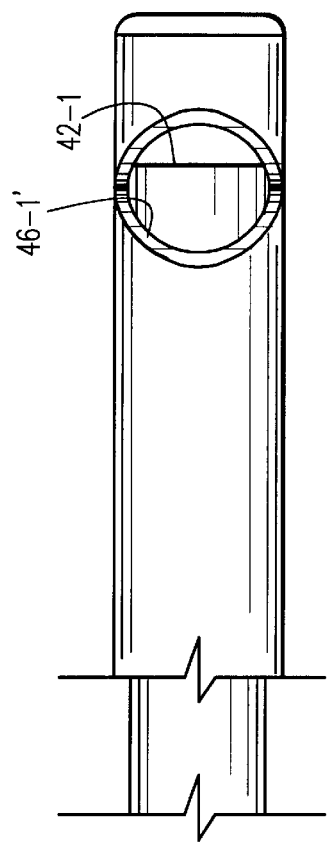
Figure 8:
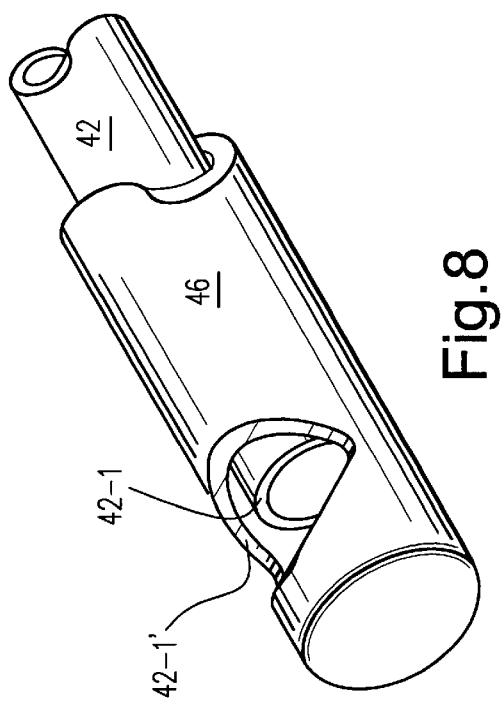
Figure 11:
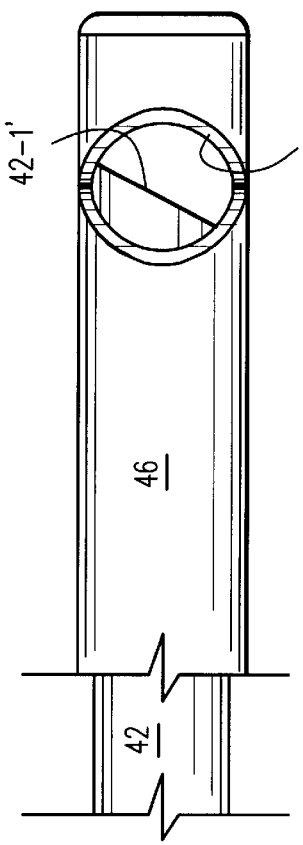
FIG. 11 is a top plan view of yet another alternative configuration for a working element that may be employed in the surgical instrument of the present invention.

In FIGS. 8–10, an alternative tip 14 is proposed whereby the opening 46-1' is generally V-shaped. In the embodiment of FIG. 11, the edge 42-1' may be beveled (angled) relative to the axis A1 of the instrument. Suffice it to say, a large number of variations in the working tip 14 may be envisioned which take advantage of the rotary and longitudinal oscillations of the interior working tube 42 as described previously.

Figure 12:
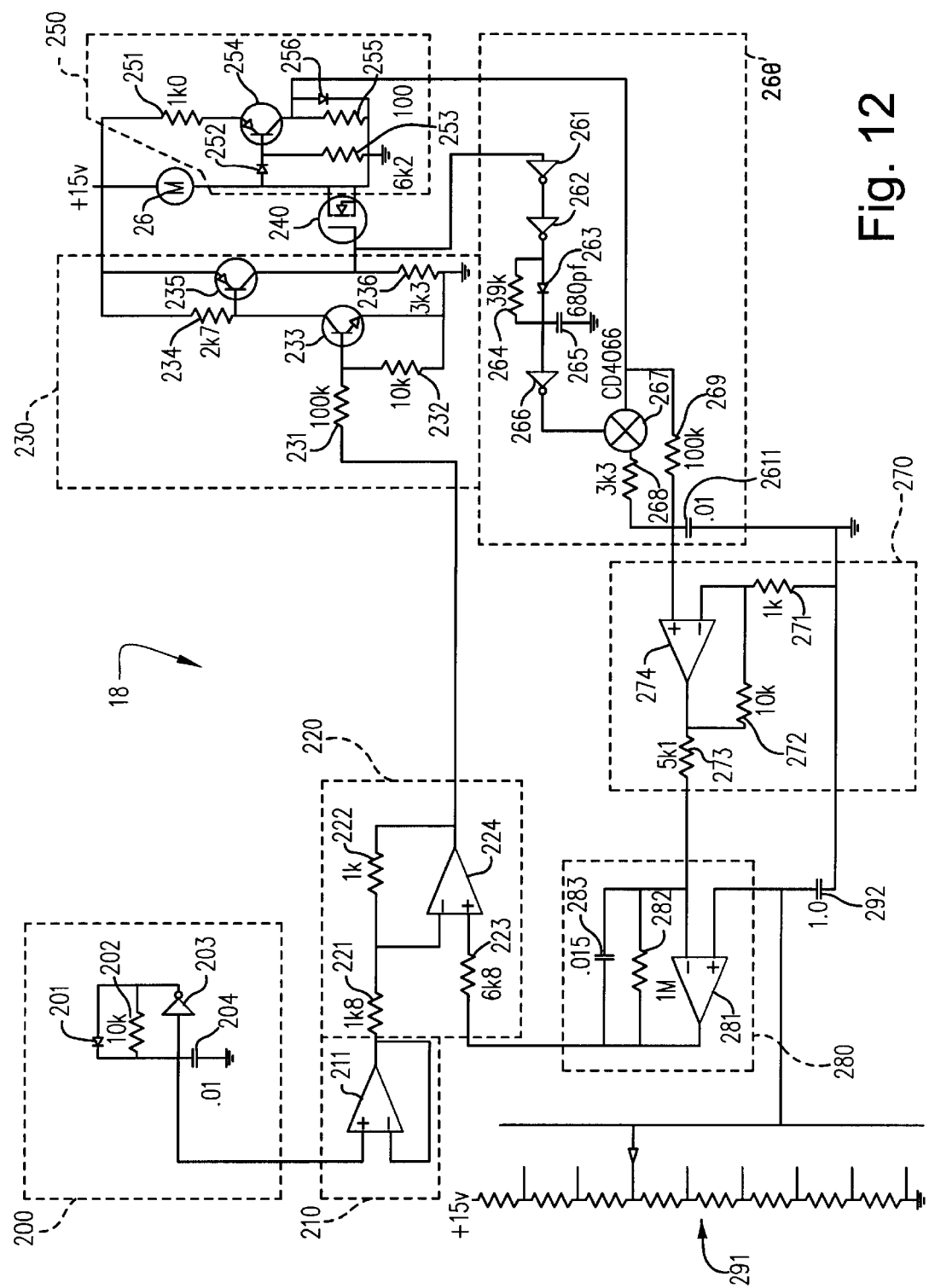
FIG. 12 is a schematic diagram of a preferred power supply circuit that may be employed in operative association with the surgical instrument in accordance with the present invention.

A particularly preferred embodiment of a power supply 18 which supplies electrical power to the instrument 10 via power cable 18-1 (see FIG. 1) in accordance with the present invention is depicted in accompanying FIG. 12. One goal of the power supply 18 is to control the speed of the motor 26. Specifically, the power supply 18 is designed to control the angular velocity (rotational velocity with respect to the longitudinal axis of the instrument 10) of the rotary drive shaft 26-1, and hence the respective angular velocities of the entire drive hub 30, drive magnet ring 32 and bearing pin 34, so that the angular velocity of the drive shaft 26-1 is maintained at a constant level. By maintaining the angular velocity of the rotary drive shaft 26-1 at a constant level, any net torque and/or vibration on the instrument 10 may be minimized.

The power supply 18 controls the angular velocity of the rotary draft shaft 26-1 by supplying variable width full voltage pulses to the motor 26 to induce a back EMF voltage therefrom. The back EMF voltage from the motor 26 is indicative of the angular velocity of the rotary drive shaft 26-1 and is sampled during the time intervals between when the pulses are supplied by the power supply 18 to the motor 26. That is, when the motor 26 is "coasting" between pulses supplied by the power supply 18, the motor 26 generates a back EMF voltage which is proportional to the angular velocity of the drive shaft 26-1. The sampled back EMF voltage is then ultimately converted to a voltage signal indicative of the back EMF voltage and compared to a set point voltage indicative of a predetermined desired angular velocity of the rotary drive shaft 26-1. If the voltage signal representing the angular velocity of the drive shaft 26-1 is different than the set point voltage, the power supply 18 changes the pulsewidth of the full voltage pulses supplied to the motor 26 so that the actual angular velocity of the rotary drive shaft 26-1, as reflected by the sampled back EMF voltage, becomes equal to the desired angular velocity as reflected by the set point voltage. Specifically, the variable width full voltage pulses supplied from the power supply 18 to the motor 26 is increased/decreased (i.e., the duty cycle is increased/decreased) as the sampled back EMF voltage decreases/increases relative to the set point voltage so that the angular velocity of the rotary drive shaft 26-1 will converge to the desired velocity. The angular velocity of the rotary drive shaft 26-1 is thus maintained at a constant desired level. As will be discussed in more detail below, by maintaining the rotary drive shaft 26-1 at a constant angular velocity, the power supply 18 will minimize the net torque and/or vibration on the instrument 10.

As shown in FIG. 12 the power supply 18 essentially includes a sawtooth waveform generator 200, a buffer 210, an inverter and DC offset circuit 220, a NPN-PNP transistor amplifier 230, a FET amplifier 240, a voltage translator and buffer 250, a voltage sampler 260, a buffer 270, a comparator 280, a switch network 291 and a capacitor 292. The motor 26 is operatively connected to the power supply 18 as shown in FIG. 12.

In the preferred embodiment, the sawtooth waveform generator 200 includes a diode 201, a 10K resistor 202, an inverter 203 and a 0.1 $\mu$f capacitor 204. The sawtooth waveform generator 200 generates a constant frequency sawtooth waveform at approximately 15 khz. Those skilled in the art will recognize, however, that this frequency can be changed simply by changing the values of the resistor 202 and the capacitor 204.

The sawtooth waveform from the generator 200 is provided to the buffer 210 which is essentially formed by an unity gain opamp 211. Specifically, the sawtooth waveform is provided to the non-inverting input of the opamp 211. The buffer 210 prevents the sawtooth waveform generator 200 from being loaded by any resistance coupled thereto.

The sawtooth waveform output from the buffer 210 is provided to the inverter and DC offset circuit 220 which includes a 1K8 resistor 221, a 1K resistor 222, a 6K8 resistor 223 and an opamp 224. While the values of the resistor 221 and resistor 222 enable the opamp 224 to produce a reduced-amplitude sawtooth waveform, those skilled in the art will appreciate that these resistor values can be varied. The sawtooth waveform provided to the inverting input of the opamp 224 is inverted and applied with a DC offset. The output of the opamp 224 will thus be an inverted representation of the sawtooth waveform input to the circuit 220 imposed on a DC level. The DC level provided on the non-inverting input of the opamp 224 through the resistor 223 can be varied (as will be discussed in more detail below) so that the output of the opamp 224 can be have a higher or lower DC level.

The signal output from the circuit 220 is provided to the NPN-PNP transistor amplifier 230 which includes a 100K resistor 231, a 10K resistor 232, a NPN transistor 233, a 2K7 resistor 234, a PNP transistor 235 and a 3K3 resistor 236. The NPN-PNP transistor amplifier 230 "squares up" the inverted sawtooth waveform input from the circuit 220. That is, the amplifier 230 amplifies the inverted sawtooth waveform from the circuit 220 and has a high enough gain so that the output of the amplifier 230 is a squarewave.

The squarewave output from the amplifier 230 is used to drive the) gate of the FET 240 to turn it on or off. The FET 240 amplifies the input squarewave to correspondingly generate variable width full voltage pulses that drive the motor 26. The pulsewidth of the voltage pulses may be increased/decreased to correspondingly increase/decrease the angular velocity of the drive shaft 26-1 of the motor 26. When the FET 240 is on and hence when a voltage pulse is being applied to the motor 26, the source voltage (15 volts in the preferred embodiment), is imposed across the motor 26. When the FET 240 turns off and hence when the motor is "coasting", a back EMF voltage of the motor 26 is generated at the junction between the FET 240 and the motor 26 with respect to the 15 volt supply. This back EMF voltage of the motor 26 is indicative of the angular velocity of the rotary drive shaft 26-1.

The voltage translator and buffer 250 includes a 1K0 resistor 251, a diode 252, a 6K2 resistor 253, a PNP transistor 254, a 100 resistor 255 and a diode 256. When the FET 240 is turned on and a voltage pulse is being applied to motor 26, the diode 252 and the resistor 253 provide a compensated signal to the base of the transistor 254 and a voltage across resistor 255 is limited by the diode 256. When the FET 240 is turned off and the motor 26 is "coasting", the diode 252 is forward biased so that the voltage across the resistor 251 is essentially the same voltage across the motor 26. The back EMF signal is generated by the motor 26 and converted to a current proportional to the back EMF voltage by the resistor 251 during the "coasting" period. This current flows through the resistor 255 and diode 256 and is converted to a voltage referenced to ground by the resistor 255. This voltage is insufficient to cause significant current to flow through diode 256. Accordingly, the voltage across the resistor 255 when the FET 240 is off is indicative of the angular velocity of the rotary drive shaft 26-1 of the motor 26.

The voltage sampler 260 includes inverters 261, 262, 266, a diode 263, a 39K resistor 264, a 680 pf capacitor 265, a CD4066 gate 267, a 3K3 resistor 268, a 100K resistor 269 and a 0.1 µf capacitor 2611. The inverters 261, 262, 266, diode 263, resistor 264 and capacitor 265 generate a delayed sampling pulse that is timed so that when the FET 240 turns off, the gate 267 is turned on. This enables the capacitor 2611 to be charged through the resistor 268 to a smoothed voltage proportional to the angular velocity of the drive shaft 26-1. The resistor 269 charges the capacitor 2611 to a voltage limited by the diode 256 when continuous power is applied to the motor 26, e.g., when there are no sampling pulses to otherwise charge the capacitor 2611. The voltage sampler 260 preferably samples the voltage proportional to the angular velocity near the end of the "coasting" interval because the length of time that the motor 26 is "coasting" varies inversely to the length of time that the motor is being powered depending on the load on the motor 26.

The signal from the voltage sampler 260, i.e., the voltage across the capacitor 2611, is provided to the buffer 270 which includes a 1K resistor 271, a 10K resistor 272, a 5K1 resistor 273 and an opamp 274. The buffer 270 amplifies the signal provided to the non-inverting input of the opamp 274 and provides an output signal which is proportional to the angular velocity of the drive shaft 26-1.

The output signal from the buffer 270 is provided to a comparator 280 which includes an opamp 281, a 1M resistor 282 and a 0.015 µf capacitor 283. Specifically, the signal from the buffer 270 is provided to the inverting input terminal of the opamp 281. The non-inverting input of the opamp 281 is operatively connected to a switching network 291 which provides a set point voltage indicative of a predetermined desired rotational velocity of the drive shaft 26-1.

The difference between the voltages on the inputs of the opamp 281 is amplified and filtered by the opamp 281, resistor 282 and capacitor 283 and applied to the non-inverting input of the opamp 224 of circuit 220 through the resistor 223. If a voltage difference exists between the inputs of the comparator 280, the DC offset applied to the opamp 224 will be changed such that the output of the opamp 224 has a different DC offset. This adjusted DC offset is then applied to the NPN-PNP transistor amplifier 230 which in turn will increase or decrease the duration of the pulsewidth of the voltage pulses provided by the FET 240 to the motor 26 (as needed) to ultimately eliminate the difference between the actual angular velocity of the drive shaft 26-1 and its desired angular velocity as reflected by the set point voltage. Thus, the difference between the voltages compared by opamp 281 will ultimately become zero.

If there is thus a difference between the desired angular velocity of the drive shaft 26-1 and its actual angular velocity, the DC offset level is changed so that the angular velocity of the drive shaft 26-1 is increased or decreased to eliminate the difference. An increase/decrease in the DC offset input to the opamp 224 through the resistor 223 will ultimately increase/decrease the pulsewidth (i.e., duty cycle) of pulses provided to the motor 26 by the FET 240 and hence increase/decrease the angular velocity of the drive shaft 26-1. The DC level provided to the opamp 224, the duty cycle of the FET 240, and the angular velocity of the drive shaft 26-1 are therefore directionally proportional. The velocity of the motor for a given duty cycle varies inversely with the load.

The sampling frequency and filter time constants of power supply 18 are selected so that the changes in the duty cycle, and hence power to the motor 26 occur more quickly than the time required for a single rotation of the drive shaft 26-1 of the motor 26 to thereby compensate for any cyclic loading imposed on the drive shaft 26-1. This decreases the vibration of the instrument 10.

Accordingly, the voltage translator and buffer 250, voltage sampler 260 and buffer 270 effectively sense and provide a voltage indicative of the angular velocity of the drive shaft 26-1. This voltage is then used by the comparator 280, inverter and DC offset circuit 220 and NPN-PNP transistor amplifier 230 and FET 240 to essentially provide a negative feedback control of the speed of the motor 26.

As described in detail above, the magnet ring 32 may be rotated continuously by virtue of the driven interconnection with the drive shaft 26-1 of the motor 26 through the drive hub 30. The magnet force interactions between the drive magnet ring 32 and the driven magnet assembly 36 will cause the later to have both simultaneous rotational and longitudinal oscillations to be imparted to the driven magnet assembly 36 and structures fixed thereto. The moving parts of the motor 26, hub 30, elastomeric washer 30-4, pin 34 and drive magnet ring 32 of the instrument 10 are coupled tightly so that they can essentially be viewed as a single mass (hereinafter referred to as the "drive"). Working tip 14 contains the driven magnet assembly 36, transition tube 38, bushing 39, working tube 42, retaining ring 52 and a portion of flexible tube 20-1 and resilient coupling 50 to the extent that the portions of tube 20-1 and resilient disk 50 move together with the aforementioned components that move together as a single mass, and will hereinafter referred to as the "driven tip assembly". The instrument 10 can thus be viewed to include two main moving masses, the drive and the driven tip assembly and two forces coupled thereto, the torque caused by the rotary movement of the drive and the force imposed by the resilient coupling 50.

The electric power from the power supply 18 will enable the drive to rotate, thereby moving the resilient coupling 50 forward. Energy is thus stored in the coupling 50 as the force on the coupling 50 increases. This increased force provided by the coupling 50 tends to slow the angular velocity of the drive. The power supply 18 senses this tendency of the drive and increases the power applied to the motor 26 (as discussed above) in order to maintain a constant angular velocity of the drive at a desired level. The increased force imposed on the drive by the coupling 50 is thus opposed and balanced by the force resulting from the increased power supplied from the power supply 18 to the motor 26. A net torque and/or vibration on the instrument 10 can thus be minimized.

When the drive magnet ring 32 and the driven magnet assembly 36 decouple, the driven tip assembly starts to turn in the reverse direction and starts to move forward axially. This movement decreases the force applied onto the resilient coupling 50 proportionally to the reverse rotation. The drive is therefore relieved of the load imposed by the coupling 50 and will tend to thus increase its angular velocity. However, the power supply 18 will sense this tendency and quickly (i.e., at least less than the time required for the drive to rotate once) decrease the electric power to the motor 26. Again, this control by the power supply 18 will maintain balanced, opposing forces on the instrument 10 and therefore minimize the net torque and vibration thereon.

In much the same manner, any external force which will tend to increase or decrease the angular velocity of the drive (with respect to a stator of the motor 26 or housing of the instrument 10) can be sensed by the power supply 18 which will respond by quickly (i.e., at least less than the time required for the drive to rotate once) changing the power to the motor 26 to balance the external force. As described above, this change in power provided to the motor 26 will generate a force that opposes the external force and thus decrease any vibration caused therefrom.

In the preferred embodiment illustrated in FIG. 12, the type of NPN transistor is 2N222, the type of PNP transistors is 2N2907 and the type of FET is IRFD120. The type of diodes is 1N914, the type of inverters is CD40106 and the type of opamps is LM324. Those skilled in the art will readily appreciate, however, that suitable replacements are available.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A magnetic coupling comprising:
   drive and driven magnet assemblies having magnetically cooperative permanent magnets which magnetically couple said drive and driven magnet assemblies one to another,
   said magnetically cooperative permanent magnets being arranged in such a manner to translate continuous rotation of said drive magnet assembly about a drive axis into simultaneous rotary and longitudinal oscillations of said driven magnet assembly relative to said drive axis, wherein
   said driven magnet assembly includes at least one permanent driven magnet, and wherein said drive magnet assembly includes an annular drive ring surrounding said driven magnet assembly which includes at least one pair of circumferentially and longitudinally spaced apart drive magnets.

2. The magnetic coupling as in claim 1, further comprising a resilient coupling member exhibiting torsional and longitudinal resiliency which is connected operatively to said driven magnet assembly to allow for said simultaneous rotary and longitudinal oscillations thereof.

3. The magnetic coupling as in claim 2, further comprising drive and output shafts coaxially aligned with one another along said drive axis and connected operatively to said drive and driven magnet assemblies, respectively.

4. The magnetic coupling as in claim 3, further comprising a housing for housing said drive and driven magnet assemblies therewith, and an elastomeric disc is connected to and between said output shaft and an interior region of said housing.

5. The magnetic coupling as in claim 4, wherein said housing includes an annular bearing assembly which supports said drive magnet assembly for rotational movement within said housing.

6. The magnetic coupling as in claim 5, wherein said drive magnet assembly includes a drive hub having one end portion which carries said drive ring and an opposite end portion which is rotatably supported by said annular bearing assembly.

7. The magnetic coupling as in claim 6, wherein said output shaft is tubular, and wherein said drive hub includes a bearing pin having (i) a first end which is immovably fixed to said opposite end portion of said drive hub and extends outwardly therefrom along said drive axis and through said driven magnet assembly, and (ii) a second end portion which is rotatably received within said tubular output shaft.

8. The magnetic coupling as in claim 2, wherein said resilient coupling member includes an elastomeric disc.

9. The magnetic coupling as in claim 2, wherein said resilient coupling member includes an elastomeric conically shaped section.

10. The magnetic coupling as in claim 9, wherein said resilient coupling member includes inner and outer tubular sections each joined at distal end regions thereof to said conically shaped section.

11. A magnetic coupling comprising:
a drive shaft;
an output shaft coaxially aligned with said drive shaft relative to a drive axis;
drive and driven magnet assemblies connected operatively to said drive and output shafts, respectively, and having permanent magnets arranged to translate continuous rotation of said drive shaft into simultaneous rotary and longitudinal movements of said driven magnet assembly relative to said drive axis;
a resilient support member exhibiting torsional and longitudinal resiliency which is operatively connected to said output shaft to allow for said simultaneous rotary and longitudinal movements thereof; and
a housing defining an interior space for housing said drive and output shafts and said drive and driven magnet assemblies, wherein
said resilient support member includes an elastomeric disc having inner and outer annulus regions connected immovably to said output shaft and said housing, respectively.

12. The magnetic coupling of claim 11, wherein said elastomeric disc is formed of a silicone rubber or butyl rubber material.

13. The magnetic coupling of claim 11, wherein said drive magnet assembly includes an annular bearing assembly, a drive ring, and a drive hub, wherein said drive hub has one end portion which carries said drive ring and an opposite end portion which is rotatably supported within said housing by said annular bearing assembly.

14. The magnetic coupling of claim 13, wherein said output shaft is tubular, and wherein said drive hub includes a bearing pin having (i) a first end which is immovably fixed to said opposite end portion of said drive hub and extends outwardly therefrom along said drive axis and through said driven magnet assembly, and (ii) a second end portion which is rotatably received within said tubular output shaft.

15. A magnetic coupling comprising:
(i) a driven magnet assembly having at least one driven magnet; and
(ii) a drive magnet assembly having an annular drive ring coaxially surrounding said driven magnet assembly, wherein said drive magnet assembly includes at least one pair of circumferentially and longitudinally spaced apart drive magnets; wherein
(iii) said drive magnets and said at least one driven magnet being arranged in such a manner to translate continuous rotation of said drive magnet assembly about a drive axis into simultaneous rotary and longitudinal oscillations of said driven magnet assembly relative to said drive axis.

16. The magnetic coupling of claim 15, further comprising a drive hub having one end which is immovably fixed to said annular drive ring so that said drive hub and said drive ring rotate as a unit about said drive axis.

17. The magnetic coupling of claim 16, wherein said drive hub includes an annular bearing assembly operatively connected to another end thereof for supporting said drive hub for rotational movement in a predetermined direction about said drive axis.

18. The magnetic coupling of claim 16 or 17, wherein said driven magnet assembly includes a tubular output shaft extending outwardly therefrom along said drive axis, and a central aperture coaxially aligned with said lumen, and wherein said drive hub includes a bearing pin having one end fixed to said drive hub and another end movably received within said lumen of said tubular output shaft, said bearing pin extending through said central aperture of said driven magnet assembly between said one and another ends thereof.

19. The magnetic coupling of claim 18, further comprising a housing defining an interior space for housing said drive and driven magnet assemblies, and a resilient elastomeric disc having inner and outer annulus regions connected immovably to said output shaft and said housing, respectively, to support said output shaft for simultaneous reciprocal rotary and longitudinal movements relative to said central drive axis.

20. A magnetic coupling comprising:
a drive shaft;
an output shaft coaxially aligned with said drive shaft along a drive axis; and
magnetic coupling means which magnetically couples said drive and output shafts for translating rotary movements of said drive shaft into simultaneous reciprocal rotary and longitudinal movements of said output shaft relative to said drive axis: wherein
said magnetic coupling means includes resilient coupling means for resiliently supporting said output shaft to allow for said simultaneous reciprocal rotary and longitudinal movements thereof, and wherein
said resilient coupling means includes an annular elastomeric support member exhibiting both torsional and longitudinal resiliency.

21. The magnetic coupling of claim 20, wherein said magnetic coupling means includes a driven magnet assembly rigidly connected to said output shaft, and an annular drive magnet assembly surrounding said driven magnet assembly and rigidly connected to said drive shaft.

22. The magnetic coupling of claim 21, wherein said driven magnet assembly includes at least one permanent drive magnet, and wherein said drive magnet assembly includes an annular drive ring surrounding said driven magnet assembly which includes at least one pair of circumferentially and longitudinally spaced apart drive magnets.

23. A magnetic coupling comprising:
(i) a driven magnet assembly having at least one driven magnet;
(ii) a drive magnet assembly having an annular drive ring coaxially surrounding said at least one driven magnet assembly which includes at least one pair of circumferentially and longitudinally spaced apart drive magnets;
(iii) a drive hub having one end which is immovably fixed to said annular drive ring so that said drive hub and said drive ring rotate as a unit about a central drive axis thereof, wherein (iv) said drive hub includes an annular bearing assembly operatively connected to another end thereof for supporting said drive hub for rotational movement in a predetermined direction about said central drive axis.

24. The magnetic coupling of claim 23, wherein said driven magnet assembly includes a tubular output shaft which defines a lumen and which extends outwardly therefrom along said central drive axis, and a central aperture coaxially aligned with said lumen, and wherein said drive hub includes a bearing pin having one end fixed to said drive hub and another end movably received within said lumen of said tubular output shaft, said bearing pin extending through said central aperture of said driven magnet assembly between said one and another ends thereof.

25. The magnetic coupling of claim 24, further comprising a housing defining an interior space for housing said drive and driven magnet assemblies, and an resilient elastomeric disc having inner and outer annulus regions connected immovably to said output shaft and said housing, respectively, to support said output shaft for simultaneous reciprocal rotary and longitudinal movements relative to said central drive axis.

\* \* \* \* \*